United States Patent
Msika et al.

(10) Patent No.: US 10,143,648 B2
(45) Date of Patent: Dec. 4, 2018

(54) **PEPTIDE AND OSIDE EXTRACT OF *SCHISANDRA* FRUIT AND IMPROVEMENT IN THE RESPONSE OF THE CUTANEOUS NEUROSENSORY SYSTEM**

(71) Applicant: LABORATOIRES EXPANSCIENCE, Paris la Défense (FR)

(72) Inventors: Philippe Msika, Versailles (FR); Caroline Baudouin, Rambouillet (FR); Stéphanie Bredif, Croisilles (FR)

(73) Assignee: LABORATOIRES EXPANSCIENCE, Paris (FR)

( * ) Notice: Subject to any disclaimer, the term of this patent is extended or adjusted under 35 U.S.C. 154(b) by 0 days.

(21) Appl. No.: 15/529,694

(22) PCT Filed: Nov. 26, 2015

(86) PCT No.: PCT/EP2015/077795
§ 371 (c)(1),
(2) Date: May 25, 2017

(87) PCT Pub. No.: WO2016/083515
PCT Pub. Date: Jun. 2, 2016

(65) Prior Publication Data
US 2017/0326061 A1 Nov. 16, 2017

(30) Foreign Application Priority Data
Nov. 26, 2014 (FR) ...................... 14 61518

(51) Int. Cl.
| A61K 36/79 | (2006.01) |
| A61K 8/97 | (2017.01) |
| A61Q 19/00 | (2006.01) |
| A61Q 7/00 | (2006.01) |
| A61Q 17/04 | (2006.01) |
| A61Q 19/08 | (2006.01) |
| A61K 36/00 | (2006.01) |

(52) U.S. Cl.
CPC ............ *A61K 8/97* (2013.01); *A61K 36/79* (2013.01); *A61Q 7/00* (2013.01); *A61Q 17/04* (2013.01); *A61Q 19/00* (2013.01); *A61Q 19/005* (2013.01); *A61Q 19/08* (2013.01); *A61K 36/00* (2013.01); *A61K 2800/78* (2013.01)

(58) Field of Classification Search
None
See application file for complete search history.

(56) References Cited

U.S. PATENT DOCUMENTS

| 6,146,616 | A | 11/2000 | Msika et al. |
| 6,582,688 | B1 | 6/2003 | Broutin et al. |
| 8,586,107 | B2 * | 11/2013 | Garnier .................. A61K 8/97 |
| | | | 424/725 |
| 8,758,833 | B2 * | 6/2014 | Garnier .................. A61K 8/602 |
| | | | 424/725 |
| 2003/0130532 | A1 | 7/2003 | Bardet et al. |
| 2004/0018258 | A1 | 1/2004 | Piccirilli et al. |
| 2004/0121030 | A1 | 6/2004 | Piccirilli et al. |
| 2006/0122246 | A1 | 6/2006 | Msika et al. |
| 2006/0216249 | A1 | 9/2006 | Msika et al. |
| 2007/0098823 | A1 | 5/2007 | Piccardi et al. |
| 2007/0116812 | A1 | 5/2007 | Msika et al. |
| 2008/0050458 | A1 | 2/2008 | Choulot et al. |
| 2008/0113921 | A1 | 5/2008 | Piccirilli et al. |
| 2008/0194476 | A1 | 8/2008 | Piccirilli et al. |
| 2009/0196837 | A1 | 8/2009 | Msika et al. |
| 2009/0286871 | A1 | 11/2009 | Msika et al. |
| 2010/0136144 | A1 | 6/2010 | Msika |
| 2012/0052142 | A1 | 3/2012 | Gnabre |
| 2012/0121725 | A1 | 5/2012 | Garnier et al. |
| 2012/0121743 | A1 | 5/2012 | Garnier et al. |

FOREIGN PATENT DOCUMENTS

| FR | 2 822 821 A1 | 10/2002 |
| FR | 2 857 596 A1 | 1/2005 |
| JP | 11-180885 A | 7/1999 |
| JP | H11 180885 | * 7/1999 |
| JP | 2000-178168 A | 6/2000 |
| JP | 2002-241293 A | 8/2002 |
| WO | WO 98/47479 A1 | 10/1998 |
| WO | WO 01/21150 A1 | 3/2001 |
| WO | WO 01/21605 A2 | 3/2001 |
| WO | WO 01/51596 A2 | 7/2001 |

(Continued)

OTHER PUBLICATIONS

Huyke C. et al. Composition and Biological Activity of Different Extracts from Schisandra sphenanthera and Schsandra chinensis. Planta Medica 73:1116-1126, 2007.*

Huyke et al., "Composition and Biological Activity of Different Extracts from Schisandra sphenanthera and Schisandra chinensis," Planta Med, vol. 73, 2007 (Published online Jul. 5, 2007) pp. 1116-1126 (Total 5 pages).

International Search Report and Written Opinion of the International Searching Authority (forms PCT/ISA/210 and PCT/ISA/237), dated Jan. 8, 2016, for International Application No. PCT/EP2015/077795, with an English translation of the International Search Report.

(Continued)

*Primary Examiner* — Ralph J Gitomer
(74) *Attorney, Agent, or Firm* — Birch, Stewart, Kolasch & Birch, LLP

(57) ABSTRACT

The present invention relates to the use of a peptide and glycoside extract of *Schizandra* fruit as a cutaneous neurosensory agent, for improving the response of the cutaneous neurosensory system, in particular for: —improving cutaneous innervation in the basal state, —combatting age-related loss of cutaneous innervation in the basal state, advantageously for preventing loss of the cutaneous sensitivity and/or combatting thinning of the epidermis, and/or —improving cutaneous perception of the environment, more particularly for combatting burns, extreme cold and/or pain.

10 Claims, 4 Drawing Sheets

(56) References Cited

FOREIGN PATENT DOCUMENTS

| | | |
|---|---|---|
| WO | WO 2004/012496 A2 | 2/2004 |
| WO | WO 2004/012752 A2 | 2/2004 |
| WO | WO 2004/016106 A1 | 2/2004 |
| WO | WO 2004/050052 A1 | 6/2004 |
| WO | WO 2004/050079 A1 | 6/2004 |
| WO | WO 2004/112741 A1 | 12/2004 |
| WO | WO 2004/112742 A2 | 12/2004 |
| WO | WO 2005/102259 A1 | 11/2005 |
| WO | WO 2005/105123 A1 | 11/2005 |
| WO | WO 2005/115421 A1 | 12/2005 |
| WO | WO 2007/005760 A1 | 1/2007 |
| WO | WO 2007/020382 A2 | 2/2007 |
| WO | WO 2007/057439 A1 | 5/2007 |
| WO | WO 2008/009709 A1 | 1/2008 |
| WO | WO 2008/080974 A1 | 7/2008 |
| WO | WO 2011/012612 A2 | 2/2011 |
| WO | WO 2011/012615 A2 | 2/2011 |

OTHER PUBLICATIONS

Onions et al., "A Taste of the Orient," Press Release, Mar. 1992, pp. 1-4, XP002945803.

Zhu et al., "Variation of the Lignan Content of Schisandra chinensis (Turcz.) Baill. and Schisandra sphenanthera Rehd. et Wits.," Chromatographia, vol. 66, No. 1/2, Jul. 2007, (Online Publication May 16, 2007), pp. 125-128.

* cited by examiner

PEPTIDE AND OSIDE EXTRACT OF *SCHISANDRA* FRUIT AND IMPROVEMENT IN THE RESPONSE OF THE CUTANEOUS NEUROSENSORY SYSTEM

FIELD OF THE INVENTION

The present invention relates to the use of a peptide and oside extract of *Schisandra* fruit as a cutaneous neurosensory agent, notably for improving the response of the cutaneous neurosensory system. Such a use is advantageously cosmetic.

PRIOR ART

There are in the world about 25 species belonging to the genus *Schisandra* (also *Schizandra*). Roughly 16 of these are from China. These shrubs originate in northern China and adjacent regions of Russia and Korea.

*Schisandra* is a dioecious plant (with distinct male and female flowers). The fruit is in the form of a hanging bunch somewhat similar to that of the currant bush. It has a naked peduncle in its upper part (about 5-10 cm) that is covered in its lower part by bright red berries, which are slightly larger, more compact and firmer than currants. The spherical seed is a few millimeters in size.

Two species are officially recognized as medicinal in China, *S. chinensis* and *S. sphenanthera*. Their berries are used in traditional Chinese medicine for treating coughs, asthma, night sweats, nocturnal emissions and chronic diarrhea. They are also used as tonics and for treating chronic fatigue.

With the botanical name *Schisandra*, this plant belongs to the class Magnoliopsida and the order Magnoliales. The botanical family is that of Schisandraceae. The term *Schisandra* used alone may refer to two different plants, namely *Schisandra chinensis* and *Schisandra sphenanthera*. These two species have long been regarded as equivalent: they could be designated according to their origin, "northern *Schisandra*" for *Schisandra chinensis* and "southern *Schisandra*" for *Schisandra sphenanthera*.

*Schisandra chinensis* is known in Chinese as pinyin, wǔ wèi zi, literally "five flavor berry." *Schisandra chinensis* is a slow-growing, wild, deciduous and arborescent vine able to reach 9 to 10 meters in height.

*Schisandra sphenanthera* Rehd. and Wils. is also called schisandre á fleurs orangèes (in France), southern *Schisandra* and lemon wood (in England), and hua thong wu wei zi and nan wu wie zi (in China).

If the fruit of *S. chinensis* has been the subject of an abundance of literature, much less work has been done on *S. sphenanthera*. Several reasons explain this discrepancy:

a poorer reputation in terms of its use according to Chinese tradition, a near absence of use in the West, a lower proportion of total neolignans compared with *S. chinensis*.

One of the major differences between the two species relates to the nature and the proportions of the neolignans contained in their respective fruits. This subfamily of chemical constituents is the great novelty of the genus *Schisandra*. The article (Huyke et al. 2007) reported a comparative study of the effects on cell proliferation of *S. chinensis* and *S. sphenanthera* extracts.

It is generally accepted that *S. sphenanthera* is medicinally inferior to *S. chinensis* and that it is useful only as an alternative source of active lignans.

Commercially, *S. sphenanthera* fruit is regarded as less expensive than that of *S. chinensis*.

Characteristics of the Fruits

Dried *Schisandra* fruit is comprised of about 20% essential oils, including 7% to 30% unsaponifiables (Huyke et al., 2007). Lignans are contained in the unsaponifiable fraction of the oils. Other active constituents include phytosterols and vitamins C and E.

*Schisandra* essential oil is rich in sesquiterpene derivatives such as d-cadinene (25.6%), g-cadinene, b-himachalene and santalol. Essential oil of *S. chinensis* fruit contains more monoterpene hydrocarbons than that of *S. sphenanthera* [Huyke et al., 2007].

*S. sphenanthera* fruit is characterized by its high deoxyschisandrin content. In contrast, its schisandrin and g-schisandrin contents are very low compared with those of *S. chinensis* seed (Zhu et al., 2007).

Fruit Extracts: Forms Used

The form most used in traditional medicine is dried fruit. In addition to its traditional use in China in a dehydrated state, *Schisandra* fruit is also used in the form of extracts obtained by extraction solvents enabling entrainment of the fruit's neolignans. The solvents mentioned in the literature are ethanol, supercritical $CO_2$ or $SC-CO_2$; (combined with a cosolvent or not) and hexane.

Several studies have attempted to compare the extraction capacities of $SC-CO_2$, chloroform, methanol and ethanol with regard to the neolignans of the fruit.

According to a recent publication, extraction of *Schisandra* fruit by $CO_2$ or $CO_2+5\%$ ethanol, or by hexane, leads to extract compositions that are quite similar in terms of neolignans. In contrast, the use of ethanol leads to poorer extraction of two neolignans, dehydroschisandrin and gomisin O, and apparently better extraction of g-schisandrin (Huyke et al., 2007).

In addition, an extraction technique was developed by Zhu et al. which made it possible to compare the quantities of lignans contained in *Schisandra chinensis* and *Schisandra sphenanthera* extracts, respectively (Zhu et al., 2007).

PRIOR ART

Many pharmacological properties of *Schisandra* fruit extracts have been reported in the literature, such as:

hepatic protection effects, known since the 1980s;

anti-HIV effects;

anti-inflammatory and antitumor activity;

increased bioavailability of certain products when ingested simultaneously.

Thus, many documents cite pharmacological compositions that comprise, among other active compounds, *Schisandra* extracts:

The application WO 2007/020382 of the company Phynova describes a composition comprising extracts from four plants including *Schisandra chinensis* or *Schisandra sphenanthera*, for treating hepatic, metabolic and/or immune disorders, and more particularly for treating hepatitis C.

The application WO 2007/005760 describes a composition comprising compounds of the family of schisandrins, gomisins and other compounds derived from *Schisandra chinensis* and *Schisandra sphenanthera* fruit extracts for treating chemotherapy-resistant cancer cells.

An article by Huyke et al. (2007) describes and compares the effects of *S. sphenanthera* and *S. chinensis* extracts on cells in culture: the proliferation of HaCaT and A431 epidermal cells is inhibited in a dose-dependent manner by these extracts, with the nonpolar extracts being more effective than the polar extracts. The authors of the study conclude that the SC—$CO_2$ extract of *Schisandra sphenanthera* could be useful in the prevention and treatment of inflammatory and hyperproliferative diseases of the skin.

None of these documents describes a particular *Schisandra* extract, and in particular a peptide and oside extract, for its activity as a neurosensory agent.

Neurosensory System and Skin

The skin is an organ the innervation of which is very dense and reaches the most superficial layers, excluding the stratum corneum. The epidermis is also characterized by numerous free nerve endings extending to the most external layers. These nerve endings come from the sensory neurons issuing from the spinal ganglia located along the spinal cord. These neurons thus have extremely long axons (sometimes longer than a meter) which transmit sensory information (tactile, heat, etc., but also pain) from the skin to the brain. Innervation density varies as a function of the region of the body. Thus, in humans, the hands and the face are highly innervated by comparison with the back or the abdomen.

The skin contains sensory nerve fibers and autonomic nerve fibers, both belonging to the peripheral nervous system (PNS). "Sensory"-type nerve endings respond to a variety of physiological stimuli, such as heat, cold, touch, mechanical distension and UV rays. Certain fibers can even be activated by a variety of chemical substances or by biological factors such as microbiological agents or plant-based proteases.

Autonomic nerve endings are responsible for automatic functions such as regulation of sweat-gland function, vasomotion, blood flow and, thereby, thermoregulation. These fibers thus have a role in homeostasis (maintenance of internal equilibrium) and are also involved in complex interactions between physiological and behavioral aspects.

Connections between the nerves and the skin are provided at the cellular level via neurotransmitters. Among these neurotransmitters, mention may be made of substance P, calcitonin gene-related polypeptide (CGRP) or pro-opiomelanocortin (POMC). These molecules, synthesized by the nerve endings but also by the skin or the immune cells, mediate the exchange of information between the skin and the nervous system. These cells express many receptors for these neurotransmitters but also enzymes capable of breaking them down (cytokines, growth factors, etc.). Neurotransmitters are thus capable, after binding to specific receptors, of activating target skin cells such as mast cells, keratinocytes, Langerhans cells, melanocytes, Merkel cells, endothelial cells and fibroblasts. In addition, the metabolic functions of cutaneous neurons can be regulated by mediators produced by skin cells. This cellular communication, which occurs in both directions, takes part in numerous biological processes such as inflammation, the immune response, scarring, pigmentation and hair growth. The extremely tight anatomical and functional relationship between the skin and the nervous system leads us to speak in terms of a unified system: the cutaneous neurosensory system.

CGRP is a 37 amino-acid peptide produced by unmyelinated sensory nerve fibers (C-fibers), Merkel cells and autonomic nerve fibers. CGRP is capable of inducing inflammatory, vasodilator and neurotrophic effects.

Various "sensor" proteins are present on the neurons of the peripheral nervous system, which are regarded as the only transducers of cutaneous perception. Epidermal cells relay this signal transduction because they too express many sensor proteins. These proteins are chiefly transmembrane and enable the transformation of stimuli such as touch, osmotic pressure, temperature or chemical stimulations into intercellular biochemical messages. Among these proteins, which are often receptors, mention may be made of the transient receptor potential (TRP) family including heat-sensitive receptors such as transient receptor potential vanilloid 1 (TRPV1).

There thus exists a dialogue between the skin cells and the sensory neurons. These interactions take part in the sense of well-being, a homeostatic equilibrium of the epidermis, an increase in melanogenesis.

However, the anatomical location of the skin suggests that the nervous system is highly exposed to environmental challenges. The homeostasis of the cutaneous nervous system can be modified under certain conditions: aging, stress, UV rays, inflammatory pathologies, cosmetic disorders, etc. It is thus important to protect this peripheral nervous system; this "neuroprotection" is as high as the regeneration potential of the nerve tissue is low; which explains the partial recovery of sensory functions after injury, for example. During aging, this "neuroprotection" is also necessary for combating age-related neuron loss.

Preservation of the anatomical link between the central nervous system and the peripheral cutaneous sensory neurons enables preservation of good sensitivity, but also maintenance of the thermoregulation system and the sebaceous secretion system.

SUMMARY OF THE INVENTION

Peptide and oside extracts of *Schisandra* fruit are known for their use in preventing or treating skin reactions or pathologies. In particular, *Schisandra* peptide and oside extracts have activity in the treatment of acne (WO 2011/012615 and WO 2011/012612).

Unexpectedly, the inventors discovered that peptide and oside extracts of *Schisandra* fruit have cutaneous neurosensory properties that have heretofore never been described.

The present invention thus relates to the use, notably the cosmetic use, of a peptide and oside extract of *Schisandra* fruit as a cutaneous neurosensory agent, advantageously for improving the response of the cutaneous neurosensory system.

The present invention also relates to the use of a cosmetic composition comprising a peptide and oside extract of *Schisandra* fruit, as a neurosensory agent, advantageously for improving the response of the cutaneous neurosensory system.

DETAILED DESCRIPTION OF THE INVENTION

Figure 1:
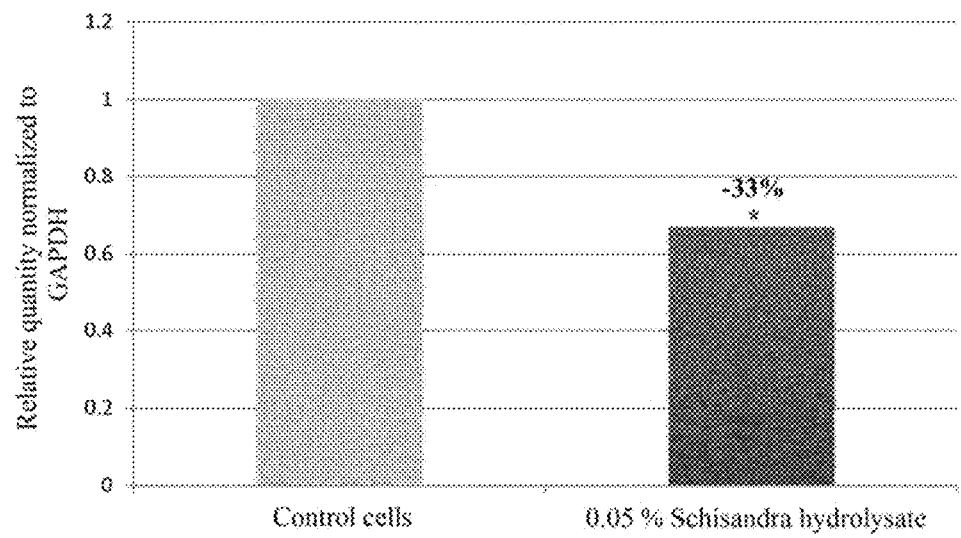
FIG. 1. Activity of a peptide and oside extract of *Schisandra Sphenanthera* on the gene expression of TRPV1 in keratinocytes. (*$p<0.05$ vs. control cells—one-way ANOVA followed by Dunnett's test)

The objective of the present invention is thus to provide an active agent for improving the response of the cutaneous neurosensory system. Such an improvement makes it possible notably to:
  enhance neuronal extension, thus improving cutaneous innervation in the basal state;
  improve the response of the cutaneous neurosensory system to environmental attacks (pain, heat, cold, etc.); and
  combat age-related loss of cutaneous innervation in order to prevent the loss of cutaneous sensitivity and to combat thinning of the epidermis.

The present invention has as an object the use of a peptide and oside extract of *Schisandra* fruit as a cutaneous neurosensory agent, notably for improving the response of the cutaneous neurosensory system.

Within the meaning of the present invention, by "neurosensory agent" is meant a compound capable of acting on the components of the cutaneous neurosensory system (nervous endings, epidermal cells, neurotransmitters, "sensory" receptors) in order to improve the response of the cutaneous neurosensory system.

Within the meaning of the present invention, by "improvement of the response of the cutaneous neurosensory system" is meant the preservation of the anatomical link between the central nervous system and the peripheral cutaneous sensory neurons. This enables a better release of nerve information in the form of neurotransmitters from keratinocytes and melanocytes and thus a better interaction between skin cells and sensory neurons. These interactions take part in the sense of well-being, in the homeostatic equilibrium of the skin, in the increase in melanogenesis, in the preservation of good sensitivity, and in the maintenance of the thermoregulation system and the sebaceous secretion system.

According to a first aspect of the invention, the present invention has as an object the use of a peptide and oside extract of *Schisandra* fruit as a neurosensory agent, for improving cutaneous innervation in the basal state, more precisely for improving cutaneous innervation density by inducing a trophic effect on neurons leading to an elongation of neuronal extensions, more particularly for improving scarring and/or for improving touch perception and/or for promoting homeostasis and thus skin comfort.

Advantageously, said peptide and oside extract of *Schisandra* fruit may be used as a massage product. In this case, said extract may be incorporated in a massage product, in particular in a massage product for babies. In an advantageous manner, the massage product comprises said peptide and oside extract of *Schisandra* fruit and a cosmetically acceptable massage excipient. More particularly, the massage product is a massage oil, notably a massage oil for babies.

Within the meaning of the present invention, by "scarring" is meant epidermal scarring, or reepithelialization, i.e., scarring of the superficial layers of the epidermis. The term "scarring" thus has a cosmetic meaning and corresponds advantageously to repair of the skin surface and/or to restructuring of the epidermis.

The absence of cutaneous sensory innervation negatively affects all scarring stages; in particular, a lack of innervation can decrease keratinocyte proliferation and induce thinning of the skin. It has been shown that sensory neurons influence reepithelialization (key stage of epidermal scarring) directly. The neurons thus enable an acceleration of scarring, without inflammation.

Furthermore, cutaneous innervation plays an important role in touch perception. By the expression "touch perception" is meant, within the meaning of the present invention, the perception of light contact with the skin, whether glabrous (hairless) or hairy. The receptors responsible for touch perception are in particular Meissner corpuscles, located in glabrous skin and situated immediately beneath the epidermis in the dermal papillae, and hair follicle receptors, which consist of free endings situated around the hair root and beneath the sebaceous glands.

According to a second aspect of the invention, the present invention has as an object the use of a peptide and oside extract of *Schisandra* fruit for combating age-related loss of cutaneous innervation in the basal state, in particular for preventing loss of cutaneous sensitivity and/or for combating thinning of the epidermis.

Indeed, the regeneration potential of nerve tissue is very low. The innervation density of the epidermis thus decreases progressively with age, thus leading to a reduction in epidermal thickness and a lack of thermal sensation due to reduced nerve density.

By the expression "cutaneous sensitivity" is meant, within the meaning of the present invention, the nerve sensitivity dependent on receptors located in the skin and stimulated by agents external to the organism. Distinguished within cutaneous sensitivity are: mechanical sensitivity (or touch perception), thermal sensitivity, and pain sensitivity (or nociception).

According to another aspect, the present invention also has as an object the use of a peptide and oside extract of *Schisandra* fruit for improving cutaneous perception of the environment, notably for avoiding excessive cutaneous reactivity and/or for combating cutaneous attacks and/or cutaneous stress from the environment, more particularly for combating burns, extreme cold, and/or pain.

The anatomical location of the skin suggests that the nervous system is highly exposed to environmental challenges; it is thus important to protect this peripheral nervous system.

Within the meaning of the present invention, the expression "cutaneous perception of the environment" means the perception of any stimulus resulting from direct contact with the external environment. In particular, these stimuli are physical, i.e., thermal, mechanical, electrical or UV radiation; chemical; or indirect, such as those produced by allergens, haptens, microbiological agents, shocks or inflammation.

Within the meaning of the present invention, by "burn" is meant any burn that can be caused by contact with a hot source, by contact with a caustic substance, by friction, by the effect of combustion, by the effect of radiation (sun-burn—ultraviolet B radiation—infrared radiation), by the effect of electric current (electrification), or by cold (frostbite).

Within the meaning of the present invention, by "extreme cold" is meant a temperature below the threshold of 0° C., advantageously below −5° C., more particularly below −10° C.

Advantageously, the present invention relates to the use of a peptide and oside extract of *Schisandra* fruit for avoiding excessive cutaneous reactivity with respect to the environment by improving cutaneous thermosensitivity and/or pain perception, and/or for combating itching and/or sensations of discomfort.

By the expression "cutaneous thermosensitivity" is meant, within the meaning of the present invention, perception by the skin of sensations of burning or of intense cold, which can lead to skin irritation reactions.

By the expression "pain perception" is meant, within the meaning of the present invention, all phenomena which allow integration into the central nervous system of a painful stimulus via activation of cutaneous nociceptors (pain receptors) and which can lead to skin irritation reactions.

Advantageously, the present invention relates to the use of a peptide and oside extract of *Schisandra* fruit for preventing or treating intolerant skin, i.e., notably for modulating the response of intolerant skin to environmental attacks.

Within the meaning of the present invention, by "intolerant skin" is meant skin having a tolerance threshold to environmental attacks that is lower than the tolerance threshold of normal skin. Intolerant skin reacts in an abnormal fashion in response to normal external stimuli generally well tolerated by "normal" skin and/or reacts to environmental attacks much more quickly than "normal" skin. "Normal" skin is skin without obvious imperfection which reacts in a controlled manner to external attacks and of which the physiology and the structure are regarded as normal. The environmental attacks may be physical, i.e., thermal, mechanical, electrical or UV radiation; chemical; or indirect, such as those produced by allergens, haptens, microbiological agents, shocks or inflammation.

This lowering of the tolerance threshold may be the consequence of cellular hyperreactivity involving epidermal, immune and nerve cells.

The reactions developed by intolerant skin to these environmental attacks may be flushing, redness (erythema), papules, pustules, telangiectasias, burning sensations, tingling, itching, red blotches, dry skin, etc.

According to another aspect, the present invention has as an object a peptide and oside extract of *Schisandra* fruit, as a neurosensory agent, or a composition comprising such an extract, for use for improving scarring, for combating itching and/or for preventing or treating intolerant skin.

Within the framework of the present invention, all the embodiments described above may be indifferently used in a separate or combined manner.

Advantageously, according to the present invention, the peptide and oside extract of *Schisandra* fruit is from *Schisandra sphenanthera*.

In a preferred embodiment of the invention, the peptide and oside extract of *Schisandra* fruit consists of:
5% to 90% peptides, and
5% to 90% total sugars,
the percentages being expressed in relation to the total weight of the dry matter of said peptide and oside extract.

The peptide and oside extract according to the invention more advantageously consists of:

10% to 50% peptides;
10% to 60% total sugars.

The peptide and oside extract according to the invention more advantageously consists of:
20% to 50% peptides;
30% to 60% total sugars.

In the present application, the terms "peptide and oside extract of *Schisandra* fruit", "peptide and oside extract of *Schisandra*" and "extract of *Schisandra*" have the same meaning and are used interchangeably to refer to the same fruit extract.

In particular, the peptide and oside extract of *Schisandra* fruit does not comprise lignans, known heretofore to be the active agents of the fruit.

According to a preferred embodiment of the invention, the peptide and oside extract of *Schisandra* fruit is advantageously obtained by a process comprising the following successive steps: starting with *Schisandra* fruit, extraction by supercritical $CO_2$ produces a crude oil and a defatted oil cake. The *Schisandra* berry oil cake, obtained after lipid extraction, is dispersed in water. Next, starch and fibers (cellulose, hemicellulose, etc.) are hydrolyzed using a mixture of cellulases and alpha-amylases and proteins are hydrolyzed by proteases. Heat treatment is used to denature the enzymes at the conclusion of the reaction. After centrifugation, the reaction medium is purified by ultrafiltration and diafiltration on a membrane having a 15 kDa cutoff in order to remove residual proteins (retentate). The permeate is then nanofiltered in order to remove mineral salts, then the peptide and oside extract is decolorized with activated carbon then filtered and collected. Finally, the product is subjected to sterile filtration (0.2 μm) and may be lyophilized or packaged. Advantageously, the product is lyophilized in the presence of maltodextrin.

TABLE 1

Example of an analytical composition of a peptide and oside extract of *Schisandra*, in percentages in relation to the dry matter:

| | |
|---|---|
| Peptide content | 13% |
| Alpha-amino nitrogen content | 6.0% |
| Total sugars content | 44% |
| Molar mass distribution of the peptides (in daltons) | |
| >3500 Da | 0% |
| 3500-1200 Da | 4% |
| 1200-300 Da | 23% |
| 300-130 Da | 18% |
| <130 Da | 55% |

The peptide and oside extract of *Schisandra* fruit may be formulated as a cosmetic composition. Thus, the present invention also relates to the use of a cosmetic composition comprising a peptide and oside extract of *Schisandra* fruit, as a neurosensory agent, advantageously for improving the response of the cutaneous neurosensory system.

Advantageously, the cosmetic composition comprising a peptide and oside extract of *Schisandra* fruit, as a neurosensory agent, may be used for:
improving cutaneous innervation in the basal state,
improving scarring,
improving touch perception, notably as a massage product,
combating age-related loss of cutaneous innervation in the basal state, advantageously for preventing loss of cutaneous sensitivity and/or for combating thinning of the epidermis, improving cutaneous perception of the environment, more particularly for combating burns, extreme cold, and/or pain, improving cutaneous thermosensitivity and/or pain perception, combating itching and/or sensations of discomfort, and/or preventing or treating intolerant skin.

The cosmetic composition may comprise from 0.01% to 15%, in particular from 0.01% to 5%, by weight of said peptide and oside extract of *Schisandra* fruit, in relation to the total weight of the composition. Such concentrations may constitute effective concentrations of the peptide and oside extract of *Schisandra* fruit.

The cosmetic composition may further contain one or more cosmetically acceptable excipient(s), such as gelling agents, for example hydrophilic or lipophilic gelling agents, preservatives, antioxidant agents, solvents, fragrances, fillers, chemical or mineral filters, pigments, chelating agents, odor absorbers, thermal spring water and/or colorants. The amounts of these various excipients are those traditionally used in cosmetics. For example, the amount of each excipient may vary from 0.01% to 20% by weight, in relation to the total weight of the cosmetic composition.

The composition according to the invention may further comprise at least one anti-inflammatory/anti-irritant agent, an antioxidant/antiradical agent, a scarring/barrier repairing agent, an anti-aging agent, and/or a moisturizing agent.

The anti-inflammatory/anti-irritant agents limit the inflammatory reaction led by cytokines or mediators of arachidonic acid metabolism and have soothing and anti-irritant properties. The most traditional are glycyrrhetinic acid (licorice derivative) and salts and esters thereof, alpha-bisabolol, *Ginkgo biloba*, Calendula, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, quinoa peptide extract, Cycloceramide® (oxazoline derivative), anti-glycation agents such as carnosine, N-acetyl-cysteine, isoflavones such as, for example, genistein/genistin, daidzein/daidzin, spring water or thermal spring water (eau d'Avène, eau de la Roche Posay, eau de Saint Gervais, eau d'Uriage, eau de Gamarde), goji extracts (*Lycium barbarum*), plant amino acid peptides or complexes, topical disulone, or anti-inflammatory medicinal products.

By "antioxidant agent" is meant a molecule that decreases or prevents the oxidation of other chemical substances. The antioxidant/antiradical agents that may be used in combination are advantageously selected from the group consisting of thiols and phenols, licorice derivatives such as glycyrrhetinic acid and salts and esters thereof, alpha-bisabolol, *Ginkgo biloba* extract, Calendula extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the family of polyphenols such as tannins, phenolic acids, anthocyanins, flavonoids such as, for example, extracts of green tea, of red berries, of cocoa, of grapes, of *Passiflora incarnata* or of *Citrus*, or isoflavones such as, for example, genistein/genistin and daidzein/daidzin. The group of antioxidants further includes anti-glycation agents such as carnosine or certain peptides, N-acetyl-cysteine, as well as antioxidant or antiradical enzymes such as superoxide dismutase (SOD), catalase, glutathione peroxidase, thioredoxin reductase and agonists thereof.

The scarring and/or barrier function repairing agents that may be used in combination are advantageously vitamin A, panthenol (vitamin B5), Avocadofurane®, avocado sugars, lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, first found in oak gall, and catechin tannins resulting from the polymerization of flavan units the model of which is provided by the catechu (*Acacia catechu*). The trace elements that may be used are advantageously selected from the group consisting of copper, magnesium, manganese, chromium, selenium, silicon, zinc and mixtures thereof.

The anti-aging agents that can act in combination to treat acne in mature subjects are antioxidants and in particular vitamin C, vitamin A, retinol, retinal, hyaluronic acid of any molecular weight, Avocadofurane®, lupin peptides and maca peptide extract.

The most commonly used moisturizers/emollients are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, monounsaturated and polyunsaturated omega-3, -6, and -7, -9 fatty acids (e.g., linoleic acid, palmitoleic acid, etc.), sunflower oleodistillate, avocado peptides and cupuacu butter.

A particularly advantageous combination according to the invention is a composition comprising the peptide and oside extract of *Schisandra sphenanthera* fruit and plant and animal unsaponifiables such as, for example, avocado and soya unsaponifiables, and unsaponifiable plant or animal oil concentrates such as, for example, sunflower or palm oil concentrates, or plant oils containing unsaponifiables such as, for example, soya and rapeseed oils, and derivatives of unsaponifiables such as avocado furans, sterol esters and vitamin derivatives.

A particularly advantageous combination according to the invention is a composition comprising the peptide and oside extract of *Schisandra sphenanthera* fruit and avocado sugars (see the application WO 2005/115421). This composition is particularly suitable for treating cutaneous barrier repair and inflammation.

A particularly advantageous combination according to the invention is a composition comprising the peptide and oside extract of *Schisandra sphenanthera* fruit and avocado peptides (see the international application WO 2005/105123). This composition is particularly suitable for treating irritation and inflammation.

Another particularly advantageous combination according to the invention is a composition comprising the peptide and oside extract of *Schisandra sphenanthera* fruit and avocado oil (see the international applications WO 2004/012496, WO 2004/012752, WO 2004/016106, WO 2007/057439).

Another particularly advantageous combination according to the invention is a composition comprising the peptide and oside extract of *Schisandra sphenanthera* fruit and Avocadofurane® (avocado furans, which may be obtained by the process described in the international application WO 01/21605). This composition is particularly suitable for treating inflammation, for promoting scarring, and for its anti-aging properties.

Another particularly advantageous combination according to the invention is a composition comprising the peptide and oside extract of *Schisandra sphenanthera* fruit and avocado and soya unsaponifiables. The avocado and soya unsaponifiables which may be used in combination are advantageously a mixture of avocado furanic unsaponifiables and soya unsaponifiables, in a ratio of roughly 1:3 to 2:3, respectively. The avocado and soya unsaponifiables are even more advantageously the product Piascledine®, sold by Laboratoires Expanscience.

Another particularly advantageous combination according to the invention is a composition comprising the peptide and oside extract of *Schisandra sphenanthera* fruit and a sunflower oleodistillate, even more advantageously a sunflower oleodistillate primarily comprising linoleic acid, such as the active agent sold by Laboratoires Expanscience, Soline® (see the international application WO 01/21150). Said composition is particularly suitable for treating inflammation and for cutaneous barrier repair.

Another particularly advantageous combination according to the invention is a composition comprising the peptide and oside extract of *Schisandra sphenanthera* fruit and a soya unsaponifiable, as obtained according to the process described in the international application WO 01/51596.

Another particularly advantageous combination according to the invention is a composition comprising the peptide and oside extract of *Schisandra sphenanthera* fruit and lupeol (FR 2 822 821, FR 2 857 596). This composition is particularly suitable for promoting scarring.

Another particularly advantageous combination according to the invention is a composition comprising the peptide and oside extract of *Schisandra sphenanthera* fruit and lupin peptides as obtained according to the process described in the application WO 2005/102259. This composition is particularly suitable for treating inflammation and is used for its anti-aging properties.

Another particularly advantageous combination according to the invention is a composition comprising the peptide and oside extract of *Schisandra sphenanthera* fruit and a total lupin extract (see the international application WO 2005/102259). This composition is particularly suitable for treating irritations.

Another particularly advantageous combination according to the invention is a composition comprising the peptide and oside extract of *Schisandra sphenanthera* fruit and lupin oil, advantageously sweet white lupin oil, such as that described in the international application WO 98/47479.

Another particularly advantageous combination according to the invention is a composition comprising the peptide and oside extract of *Schisandra sphenanthera* fruit and a maca peptide extract (see the international application WO 2004/112742). This composition is particularly valued for its scarring and anti-aging properties.

A particularly advantageous combination according to the invention is a composition comprising the peptide and oside extract of *Schisandra sphenanthera* fruit and rice peptides (see the international application WO 2008/009709). This composition is particularly valued for its melanogenesis-stimulating and melanin-transfer properties.

Another particularly advantageous combination according to the invention is a composition comprising the peptide and oside extract of *Schisandra sphenanthera* fruit and Cycloceramide® (oxazoline derivative) as described in the international applications WO 2004050052, WO 2004050079 and WO 2004112741. This composition is particularly suitable for treating inflammatory reactions.

Another particularly advantageous combination according to the invention is a composition comprising the peptide and oside extract of *Schisandra sphenanthera* fruit and a quinoa extract, in particular a peptide extract (see the international application WO 2008/080974). This composition is particularly suitable for treating inflammatory conditions and for cutaneous barrier repair.

Another particularly advantageous combination according to the invention is a composition comprising the peptide and oside extract of *Schisandra sphenanthera* fruit and cupuacu butter. This composition is particularly valued for its moisturizing properties.

Another particularly advantageous combination according to the invention is a composition comprising the peptide and oside extract of *Schisandra sphenanthera* fruit and rapeseed oleodistillate.

Another advantageous combination according to the invention is a composition comprising the peptide and oside extract of *Schisandra sphenanthera* fruit and corn oleodistillate.

All these combinations comprise at least one other active compound, in addition to the *Schisandra sphenanthera* fruit extract, and may comprise two, three, four or more active compounds as described above.

In addition to these active agents, the peptide and oside extract of *Schisandra sphenanthera* fruit according to the invention, alone or in combination with the active agents cited above, may be used in combination with sun protection active agents, such as UVB and/or UVA sun filters or screens, such as the inorganic and/or organic screens or filters known to persons skilled in the art, who will adapt their choice and their concentrations according to the degree of protection sought.

By way of examples of sun protection active agents, particular mention may be made of titanium dioxide, zinc oxide, methylene bis-benzotriazolyl tetramethylbutylphenol (brand name: TINOSORB M) and bis-ethylhexyloxyphenol methoxyphenyl triazine (brand name: TINOSORB S), octocrylene, butyl methoxydibenzoylmethane, terephthalylidene dicamphor sulfonic acid, 4-methylbenzylidene camphor, benzophenone, ethylhexyl methoxycinnamate, ethylhexyl dimethyl PABA, and diethylhexyl butamido triazone.

The composition according to the invention may be formulated as various preparations suitable for topical application, such as creams, gels, emulsions, milks, pomades, lotions, oils, aqueous or hydroalcoholic or glycolic solutions, powders, patches, sprays, or any other product for external application. Such formulations are presented in the examples below.

The following examples aim to illustrate the present invention.

EXAMPLES

Example 1: Effect of a Peptide and Oside Extract of *Schisandra Sphenanthera* on the Gene Expression of TRPV1

It is possible, in culture, to model the mechanism of antidromic action potentials. Sensory neurons, derived from spinal ganglia, are cultured in the presence of keratinocytes. After 10 days, the neurons are mature; they spontaneously release neuropeptides such as CGRP and substance P at the level of the keratinocytes. This is referred to as basal release; it can be measured by ELISA kits.

The transient receptor potential vanilloid 1 (TRPV1) receptor is a membrane protein belonging to the TRP family of nonselective cation channels. It is a nociceptor which responds to, among other things, activation by capsaicin.

In the skin, TRPV1 is expressed by keratinocytes, mast cells and nerve fibers. In response to thermal (>43° C.), chemical, or mechanical stimulation, activation of TRPV1 leads to the release of cytokines and neuropeptides leading to a neurosensory response (activation of sensory nerves) which is expressed as sensations of pain, itching, discomfort, flushing.

Activation of TRPV1 also induces activation of the vascular system, directly or indirectly, which may notably lead to a powerful vasodilatory effect.

Materials and Methods

Normal human epidermal keratinocytes were incubated for 48 hours in the presence of the peptide and oside extract of *Schisandra Sphenanthera* at a concentration of 0.05% (DM).

At the conclusion of the treatment, the culture supernatants were removed and total RNA was extracted using the extraction kit RNeasy MiniKit [Qiagen]. Total RNA was then assayed in mini-chips using the Experion™ system and the Experion RNA StdSens kit [Biorad] then reverse-transcribed to cDNA using the iScript cDNA Synthesis kit [Biorad].

The newly synthesized cDNA relating to the target gene, TRPV1, or to the reference gene, GAPDH, were selectively amplified by real-time PCR on iQ5 [Biorad] by Sybr Green technology [iQ SybrGreen kit, Biorad].

The significance of the results was confirmed by one-way analysis of variance followed by Dunnett's test (GraphPad Prism software version 5.02, GraphPad Software, San Diego, Calif., USA).

Results

The peptide and oside extract of *Schisandra Sphenanthera* at a concentration of 0.05% significantly inhibited the gene expression of TRPV1 in keratinocytes (−33%, p<0.05; FIG. 1).

Conclusion

By its inhibitory action on the TRPV1 receptor, the peptide and oside extract of *Schisandra* Sphenanthera has an action as a neurosensory agent, notably for improving cutaneous perception of the environment, notably for avoiding excessive cutaneous reactivity and/or for combating cutaneous attacks and/or cutaneous stress from the environment, more particularly for combating burns, extreme cold, and/or pain.

Example 2: Effect of a Peptide and Oside Extract of *Schisandra Sphenanthera* on TRPV1 Receptor Activity Activation of the TRPV1 receptor on sensory neurons can be evaluated by analyzing the electrical activity of sensory neurons by monitoring variations of the cytoplasmic calcium concentration.

Indeed, when cells are stimulated by capsaicin, a massive amount of extracellular calcium enters the neuronal cytoplasm in order to trigger electrical activity and to cause a massive release of neuropeptides in the extracellular space.

The variation of the level of fluorescence is analyzed by the incorporation of a calcium-dependent fluorescent probe (Fluo-4) in the cells. Thus, during the increase in calcium in the cells, the level of fluorescence increases in the cell body of the neurons. The higher this level, the higher the stimulation of the neurons.

Materials and Methods

Sensory neurons cultured in the presence of normal human epidermal keratinocytes were incubated in the presence of the peptide and oside extract of *Schisandra sphenanthera* at concentrations of 0.005%, 0.01%, 0.05% and 0.1% (DM) or the reference molecule, capsazepine, at a concentration of $10^{-5}$ M (Sigma).

After 60 minutes of pre-incubation, the fluorescent probe, Fluo-4 (Molecular probe), was added to the culture medium and the cells were incubated 30 minutes. After rinsing, the co-cultures were observed under epifluorescence for 70 seconds; 5 seconds after the beginning of the recording, the neurons (in co-culture) were stimulated by capsaicin at a concentration of $10^{-6}$ M (Sigma).

The significance of the results was confirmed by Bartlett's test.

Results

Figure 2:
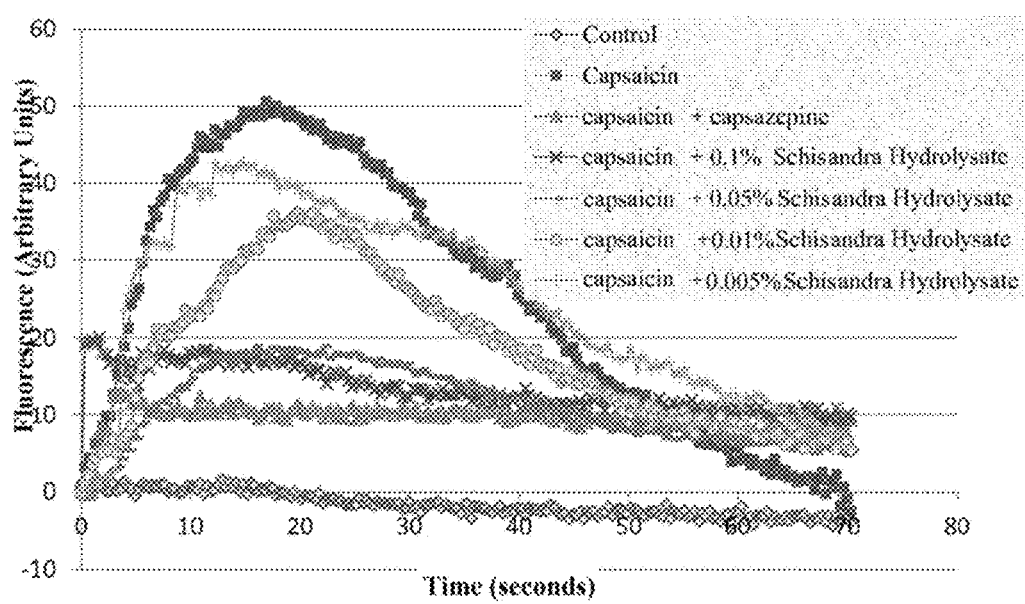
FIG. 2. Study of the effect of a peptide and oside extract of *Schisandra Sphenanthera* on intracytoplasmic calcium mobilization in sensory neurons stimulated by capsaicin in co-culture with keratinocytes: Evolution of fluorescence over time FIG. 3. Study of the effect of a peptide and oside extract of *Schisandra Sphenanthera* on intracytoplasmic calcium mobilization in sensory neurons stimulated by capsaicin in co-culture with keratinocytes: Variation of fluorescence in percentage in relation to the control. (# $p<0.05$ vs. control; * $p<0.05$, *** $p<0.001$ vs. capsaicin; Bartlett's test)
Figure 3:
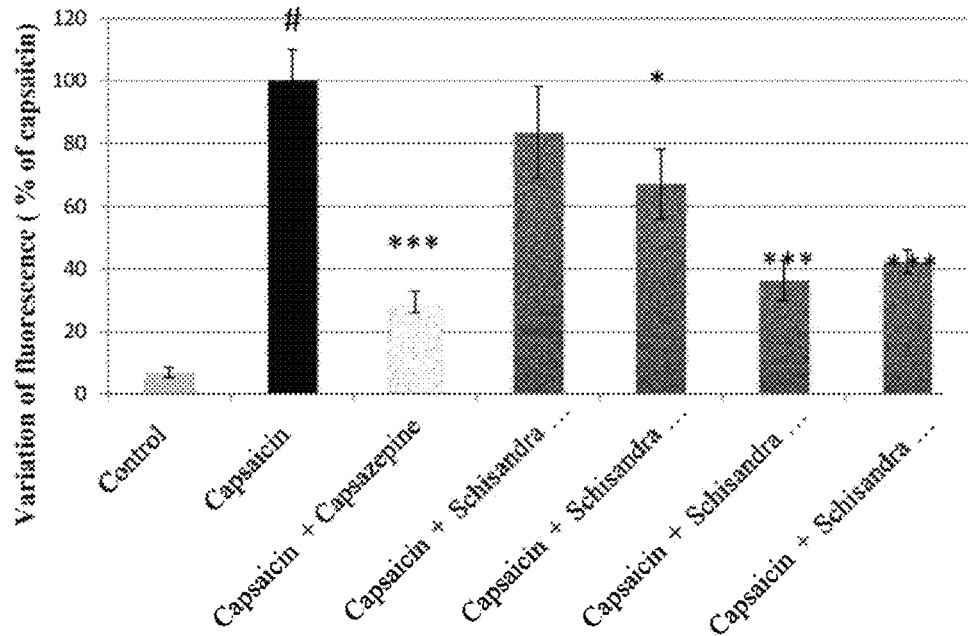

As shown in FIGS. 2 and 3, the addition of capsaicin leads to a significant increase in the level of fluorescence and thus in the quantity of intracytoplasmic calcium, reflecting activation of the TRPV1 receptor.

The peptide and oside extract of *Schisandra Sphenanthera* significantly inhibited the intracytoplasmic calcium mobilization visualized by a decrease in the variation of fluorescence. The peptide and oside extract of *Schisandra Sphenanthera* is thus capable of inhibiting TRPV1 receptor activity.

The peptide and oside extract of *Schisandra Sphenanthera* thus has an action as a neurosensory agent, notably for improving cutaneous perception of the environment, notably for avoiding excessive cutaneous reactivity and/or for combating cutaneous attacks and/or cutaneous stress from the environment, more particularly for combating burns, extreme cold, and/or pain.

Example 3: Study of the Activity of a Peptide and Oside Extract of *Schisandra Sphenanthera* on CGRP Release by Sensory Neurons Stimulated by Capsaicin in Co-Culture with Keratinocytes Capsaicin, a natural irritant of the vanilloid family, is the active constituent of a wide variety of peppers. This toxin acts chiefly on unmyelinated sensory C-fibers, notably those conveying nociceptive messages. The effect of capsaicin results from activation of a receptor called vanilloid receptor (TRPV1) present preferentially at the nerve endings of the epidermis. In the presence of capsaicin in the culture medium, the sensory neurons increase the quantity of neuropeptides released. Capsazepine is a specific antagonist of the TRPV1 receptor.

Materials and Methods

Sensory neurons were cultured in the presence of normal human epidermal keratinocytes. After 3 days of co-culture, the neurons project extensions in the form of free endings in contact with the keratinocytes.

The cells were then incubated in the presence of the peptide and oside extract of *Schisandra Sphenanthera* at concentrations of 0.005%, 0.01%, 0.05% and 0.1% (DM) or the reference molecule, capsazepine, at a concentration of $10^{-5}$ M (Sigma).

After 60 minutes of pre-incubation, the neurons (in co-culture) were stimulated by capsaicin at a concentration of $10^{-7}$ M (Sigma).

After 15 minutes of stimulation, the culture supernatants were collected in order to assay the released CGRP. The CGRP assay was carried out using the CGRP assay kit (SpiBio).

The significance of the results was confirmed by one-way analysis of variance followed by Dunnett's test.

Results

Figure 4:
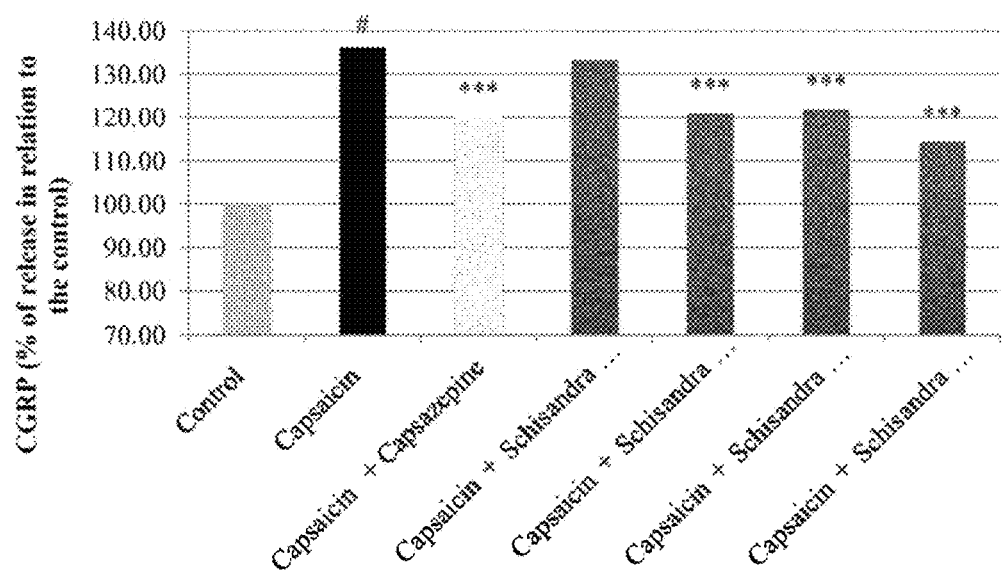
FIG. 4. Study of the activity of a peptide and oside extract of *Schisandra Sphenanthera* on the release of CGRP by sensory neurons stimulated by capsaicin in co-culture with keratinocytes. (# p<0.05 vs. control; *** p<0.001 vs. capsaicin; one-way ANOVA followed by Dunnett's test)

The peptide and oside extract of *Schisandra Sphenanthera* significantly inhibited the release of CGRP induced by capsaicin in sensory neurons in co-culture with keratinocytes (FIG. 4). This inhibitory effect is similar to that induced by capsazepine, the reference inhibitor.

Conclusion

The peptide and oside extract of *Schisandra Sphenanthera* is capable of inhibiting the TRPV1 receptor in terms of gene expression as well as in terms of activation, as shown by the inhibitory effect on CGRP release in neuron/keratinocyte co-cultures stimulated by capsaicin (specific agonist of the TRPV1 receptor).

The inhibitory effect of the peptide and oside extract of *Schisandra* Sphenanthera with respect to TRPV1 activation is comparable with that of capsazepine, a specific antagonist of TRPV1.

By its inhibitory action on the TRPV1 receptor, the peptide and oside extract of *Schisandra Sphenanthera* helps modulate the cutaneous neurosensory response, thus making it possible to improve cutaneous perception of the environment, notably for avoiding excessive cutaneous reactivity and/or for combating cutaneous attacks and/or cutaneous stress from the environment, more particularly for combating burns, extreme cold, and/or pain.

Example 4: Study of the Trophic Effect of a Peptide and Oside Extract of *Schisandra Sphenanthera* on the Development of Sensory Neuron Extensions in the Presence of Keratinocytes The length of the extensions of sensory neurons in co-culture with keratinocytes was measured at various stages of development.

Materials and Methods

Sensory neurons, cultured alone or in the presence of normal human epidermal keratinocytes, were incubated in the presence of the peptide and oside extract of *Schisandra Sphenanthera* at concentrations of 0.005%, 0.01%, 0.05% and 0.1% (DM) or the reference molecule, NGF (Sigma), at 20 ng/ml.

After 5 days of stimulation, the cells were fixed and stained with an anti-β-tubulin antibody. The analysis of the neurite network was carried out using the Developer software (GE Healthcare).

The significance of the results was confirmed by one-way ANOVA followed by Dunnett's test.

Results

Figure 5:
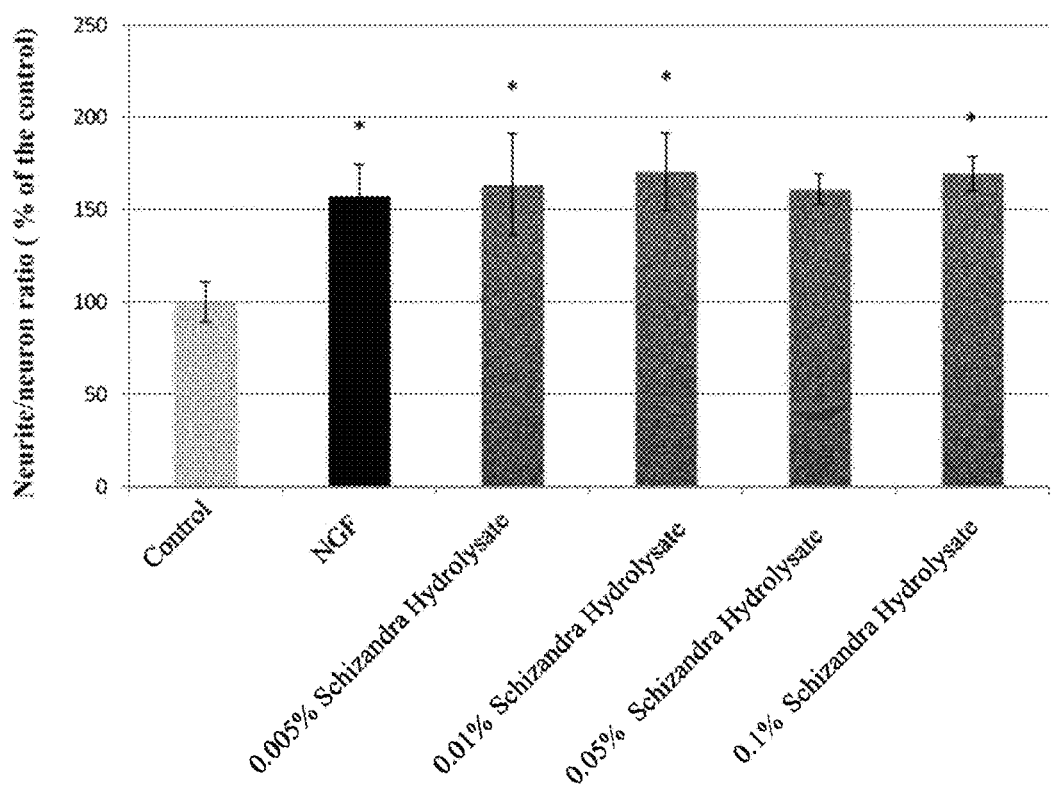
FIG. 5. Study of the trophic effect of a peptide and oside extract of *Schisandra Sphenanthera* on the development of sensory neuron extensions: neurite length for sensory neurons alone after 5 days of culture FIG. 6. Study of the trophic effect of a peptide and oside extract of *Schisandra Sphenanthera* on the development of sensory neuron extensions in the presence of keratinocytes: neurite length for sensory neurons in co-culture with keratinocytes after 5 days of culture
Figure 6:
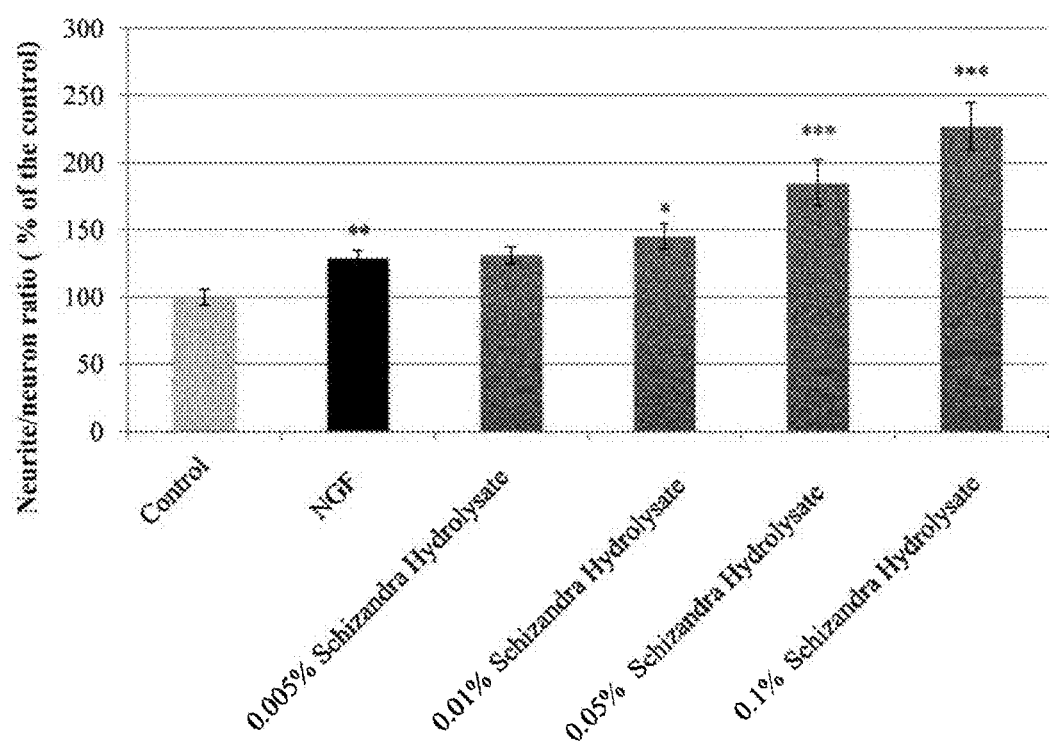

As shown in FIGS. 5 and 6, the peptide and oside extract of *Schisandra* Sphenanthera led to a significant increase in the length of the neuronal extensions. This trophic effect is potentiated in the presence of keratinocytes and, indeed, under co-culture conditions, the increase observed is greater and dose-dependent; the peptide and oside extract of *Schisandra Sphenanthera* can thus induce an increase in neurotrophic factors by keratinocytes.

The peptide and oside extract of *Schisandra Sphenanthera* thus has an action as a neurosensory agent for improving cutaneous innervation in the basal state.

Conclusion

The peptide and oside extract of *Schisandra Sphenanthera* is capable of inhibiting the TRPV1 receptor in terms of gene expression as well as in terms of activation, as shown by the effect on cytoplasmic calcium mobilization as well as the inhibitory effect on CGRP release in neuron/keratinocyte co-cultures stimulated by capsaicin (specific agonist of the TRPV1 receptor).

The inhibitory effect of the peptide and oside extract of *Schisandra Sphenanthera* with respect to TRPV1 activation is comparable with that of capsazepine, a specific antagonist of TRPV1.

By its inhibitory action on the TRPV1 receptor, the peptide and oside extract of *Schisandra Sphenanthera* helps modulate the cutaneous neurosensory response.

In addition, by the positive trophic effect exerted on sensory neurons, the peptide and oside extract of *Schisandra Sphenanthera* exerts a beneficial effect on the quality of cutaneous innervation.

Example 5: Examples of Cosmetic Formulations

Oil-in-Water EMULSION No. 1

| Raw material/Trade name | % |
| --- | --- |
| HYDROGEN POLYDECENE | From 5 to 20% |
| LAURYLGLUCOSIDE-GLYSTEARATE | From 1 to 5% |
| DICAPRYLYL CARBONATE | From 1 to 5% |
| GLYCEROL | From 5 to 20% |
| CARBOPOL | From 0 to 1% |
| XANTHAN GUM | From 0 to 1% |
| EXTRACT OF *SCHISANDRA* | From 0.01 to 5% |
| SODIUM HYDROXIDE | From 0 to 1% |
| PRESERVATIVES | From 0 to 1% |
| CITRIC ACID | From 0 to 1% |
| PURIFIED WATER | Q.S. to 100% |

Oil-in-Water EMULSION No. 2

| INCI EU | % INCI |
| --- | --- |
| AQUA | Q.S. |
| GLYCERIN | 1 to 10% |
| PROPANEDIOL DICAPRYLATE | 1 to 10% |
| DICAPRYLYL CARBONATE | 1 to 10% |
| GLYCERYL STEARATE CITRATE | 1 to 5% |
| CETYL ALCOHOL | 1 to 5% |
| XANTHAN GUM | 0 to 2% |
| EXTRACT OF *SCHISANDRA* | From 0.01 to 5% |
| TOCOPHEROL | 0 to 0.5% |
| PRESERVATIVES | 0 to 2% |
| pH ADJUSTER | 0 to 1% |
| | 100.000000 |

Water-in-Oil EMULSION

| Raw material/Trade name | % |
| --- | --- |
| LIQUID ISOPARAFFIN | From 5 to 20% |
| ISOCETYL STEARATE | From 5 to 20% |
| AL-MG HYDROXYSTEARATE | From 5 to 20% |
| ABIL WE 09 | From 1 to 5% |
| GLYCEROL | From 1 to 5% |
| VASELINE OIL | From 1 to 5% |

-continued

| Raw material/Trade name | % |
|---|---|
| MICRONIZED ZINC OXIDIZE | From 1 to 5% |
| BUTYLENE GLYCOL | From 1 to 5% |
| EXTRACT OF *SCHISANDRA* | From 0.01 to 5% |
| ISONONYL ISONONANOATE | From 1 to 5% |
| BEESWAX | From 1 to 5% |
| SODIUM TARTRATE | From 1 to 5% |
| SODIUM CHLORIDE | From 0 to 5% |
| GLYCINE | From 1 to 5% |
| PRESERVATIVES | From 0 to 1% |
| CHOLESTEROL | From 0 to 1% |
| PHYTOSPHINGOSINE | From 0 to 1% |
| TARTARIC ACID | From 0 to 1% |
| PURIFIED WATER | Q.S. to 100% |

The invention claimed is:

1. A method for improving a response of the cutaneous neurosensory system by improving the cutaneous innervation in the basal state in a subject in need thereof, comprising administering to the subject an effective amount of a peptide and oside extract of *Schisandra* fruit as a cutaneous neurosensory agent,
wherein said peptide and oside extract of *Schisandra* fruit consists of:
10% to 50% peptides, and
10% to 60% total sugars,
the percentages being expressed in relation to the total weight of said peptide and oside extract.

2. The method according to claim 1, wherein scars are reduced.

3. The method according to claim 1, wherein touch perception is increased.

4. The method according to claim 1, wherein age-related loss of cutaneous innervation in the basal state is inhibited.

5. The method according to claim 1, wherein cutaneous perception of the environment is increased.

6. The method according to claim 5, wherein cutaneous thermosensitivity and/or pain perception is increased.

7. The method according to claim 1, wherein said administering is through topical application.

8. The method according to claim 3, wherein said peptide and oside extract of *Schisandra* fruit is administered as a massage product.

9. The method according to claim 4, wherein said inhibition of age-related loss of cutaneous innervation in the basal state prevents loss of cutaneous sensitivity and/or inhibits thinning of the epidermis.

10. The method of claim 1, wherein the cuticle of the subject wherein the cutaneous neurosensory agent is administered is not inflamed.

* * * * *